United States Patent
Lee et al.

(10) Patent No.: US 9,944,965 B2
(45) Date of Patent: Apr. 17, 2018

(54) BIOSYNTHESIS OF OLIGOSACCHARIDES

(71) Applicants: The Board of Trustees of the University of Illinois, Urbana, IL (US); Seoul National University of R&DB Foundation, Seoul (KR)

(72) Inventors: Won-Heong Lee, Seoul (KR); Panchalee Pathanibul, Champaign, IL (US); Josh Quarterman, Urbana, IL (US); Michael J. Miller, Champaign, IL (US); Yong-Su Jin, Champaign, IL (US); Jin-Ho Seo, Seoul (KR)

(73) Assignees: The Board of Trustees of the University of Illinois, Urbana, IL (US); Seoul National University R&DB Foundation, Seoul (KR)

( * ) Notice: Subject to any disclaimer, the term of this patent is extended or adjusted under 35 U.S.C. 154(b) by 197 days.

(21) Appl. No.: 14/136,466

(22) Filed: Dec. 20, 2013

(65) Prior Publication Data
US 2017/0152538 A1   Jun. 1, 2017

Related U.S. Application Data

(60) Provisional application No. 61/740,118, filed on Dec. 20, 2012.

(51) Int. Cl.
| | |
|---|---|
| *C12N 9/10* | (2006.01) |
| *C12N 15/00* | (2006.01) |
| *C12N 1/20* | (2006.01) |
| *C12P 19/00* | (2006.01) |
| *C07H 21/04* | (2006.01) |
| *C12P 19/18* | (2006.01) |

(52) U.S. Cl.
CPC ............ *C12P 19/18* (2013.01); *C12N 9/1051* (2013.01); *C12P 19/00* (2013.01); *C12Y 204/01069* (2013.01)

(58) Field of Classification Search
CPC .......... C12N 9/1051; C12N 9/90; C12N 9/88; C12N 9/006; C12N 9/1241; C12N 15/70
See application file for complete search history.

(56) References Cited

U.S. PATENT DOCUMENTS

| | | | |
|---|---|---|---|
| 6,979,564 B2 * | 12/2005 | Glucksmann ........ | C07K 14/705 435/193 |
| 2004/0058418 A1 * | 3/2004 | Endo .................... | C12N 9/1051 435/101 |
| 2012/0208181 A1 * | 8/2012 | Merighi ................ | C12N 9/00 435/6.1 |

FOREIGN PATENT DOCUMENTS

CN         102120999        *  7/2011

OTHER PUBLICATIONS

Maqalhaes. Helicobacter pylori adhesion to gastric epithelial cells is mediated by glycan receptors. Braz J Med Biol Res. Jul. 2010;43(7):611-8. Epub Jun. 7, 2010.*
Jia. CN 102120999A. Machine Translation. Retrived via espacenet. com on Mar. 29, 2017.*
Rouquier. Molecular cloning of a human genomic region containing the H blood group alpha(1,2)fucosyltransferase gene and two H locus-related DNA restriction fragments. Isolation of a candidate for the human Secretor blood group locus. J Biol Chem. Mar. 3 1995;270(9):4632-9.*
Griffiths. Expressing Eukaryotic Genes in Bacteria. Modern Genetic Analysis. 1999.*
Expasy. 1.1.1.271. retrieved via http://enzyme.expasy.org/EC/1.1.1. 271 on Oct. 2, 2017.*
Albermann et al., "Synthesis of the milk oligosaccharide 2'-fucosyl-lactose using recombinant bacterial enzymes", Carbohydrate Research, 334:97-103 (2001).
Drouillard et al., "Large-Scale Synthesis of H-Antigen Oligosaccharides by Expressing Helicobacter pylori a1,2-Fucosltransferase in Metabolically Engineered *Escherichia coli* Cells", Angew. Chem., 118:1810-1812 (2006).
Dumon et al., "In ivo fucosylation of lacto-N-neotetraose and lacto-N-neohexaose by heterologous expression of Heicobacter pylori a-1,3 fucosyltransferase in engineered *Escherichia coli*", Glycoconjugate Journal, 18:465-474 (2001).
Lee et al., "Enhanced production of GDP-L-fucose by overexpression of NADPH regenerator in recombinant *Escherichia coli*", Appl Microbiol Biotechnol 91:967-976 (2011).
Byun et al., "Production of GDP-L-fucose, L-fucose donor for fucosyloligosaccharide synthesis, in recombinant *Escherichia coli*", App Microbiol Biotechnol, 74:768-755 (2007).
Stelling et al., "Metabolic network structure determines key aspects of functionality and regulation", Nature, 420:190-192 (2002).
Klamt et al., "Alogorithmic approaches for computing elementary modes in large biochemical reaction networks", IEE Proc.-Syst. Bio., 152(4):249-255 (2005).
Dumon et al., "Assessment of the Two Helicobacter pylori a-1,3-Fucosyltransferase Ortholog Genes for the Large-Scale Synthesis of LewisX Human Milk Oligosaccharides by Metabolically Engineered *Escherichia coli*", Biotechnol. Prog., 20:412-419 (2004).
Fierfort et al., "Genetic engineering of *Escherichia coli* for the economical production of sialylated oligosaccharides", Journal of Biotechnology, 134:261-265 (2008).
Lee, "High cell-density culture of *Escherichia coli*", Trends in Biotechnology, 14(3):98-105 (1996).
Zhao et al., "Global metabolic response of *Escherichia coli* to gnd or zwf gene-knockout, based on 13C-labeling experiments and the measurement of enzyme activities", Appl Microbiol Biotechnol, 64:91-98 (2004).

(Continued)

*Primary Examiner* — Yong D Pak
(74) *Attorney, Agent, or Firm* — McDonnell Boehnen Hulbert & Berghoff LLP

(57) ABSTRACT

The present invention relates to methods for production of 2'Fucosyllactose by a microbial system comprising a α-1,2 fucosyltransferase (FucT2) polynucleotide and a Guanosine 5'-diphospho-β-L-fucose (GDP-L-fucose) synthesis pathway using lactose as a substrate. Furthermore, the present invention relates to compositions comprising the microbial system.

22 Claims, 9 Drawing Sheets

(56) References Cited

OTHER PUBLICATIONS

Stevenson et al., "Organization of the *Escherichia coli* K-12 Gene Cluster Responsible for Production of the Extracellular Polysaccharide Colanic Acid", Journal of Bacteriology, 178(16):4885-4893 (1996).
Ruffing et al., "Metabolic engineering of microbes for oligosaccharide and polysaccharide synthesis", Microbial Cell Factories, 5:25 (2006).
Lee et al., "Modulation of guanosine 5'-diphosphate-D-mannose metabolism in recombinant *Escherichia coli* for production of guanosine 5'-diphosphate-L-fucose", Bioresource Technology, 100:6143-6148 (2009).
Lee et al., "Modulation of guanosine nucleotides biosynthetic pathways enhanced GDP-L-fucose production in recombinant", App Microbiol Biotechnol, 93:2327-2334 (2012).
Wang et al., "Novel Helicobacter pylori a1,2-fucosyltransferase, a key enzyme in the synthesis of Lewis antigens", Microbiology, 145:3245-3253 (1999).
Urbanczik et al., "An improved algorithm for stoichiometric network analysis: theory and applications", Bioinformatics, 21(7):1203-1210 (2005).

\* cited by examiner

List of primers and plasmids

| Name | Sequence of PCR primers and description for plasmids | Source |
|---|---|---|
| PCR primers | | |
| fucT2_F (NcoI) | 5'-ACATGCCATGGCTTTTAAGGTGGTGCAA-3'<br>SEQ ID NO:1 | H. pylori 26695 (ATCC 700392) |
| fucT2_R (SacI) | 5'-AGTCCGAGCTCTTAAGCGTTATACTTTTGGGA-3'<br>SEQ ID NO:2 | |
| Plasmids | | |
| pETDuet-1 | two T7 promoters with two MCS, pBR322 replicon (copy number ~40), Amp$^r$ | Merck Biosciences |
| pCOLADuet-1 | two T7 promoters with two MCS, ColA replicon (copy number 10 ~ 12), Kan$^r$ | Merck Biosciences |
| pmBCGW | derived from pETDuet-1, P$_{T7}$-manB-manC ( NcoI/ SacI)-P$_{T7}$-gmd-wcaG ( NdeI/ XhoI)-T$_{T7}$, Amp$^r$ | Lee et al., 2009 |
| pHfucT2 | derived from pCOLADuet-1, P$_{T7}$- fucT2 ( NcoI/ SacI)-P$_{T7}$-MCS2-T$_{T7}$, Kan$^r$ | this study |

Figure 6

Summary of batch fermentations of *E. coli* strains producing 2-FL from lactose

| Strains | Plasmids | Initial lactose concentration (g/l) | Maximum dry cell mass (g/l) | Maximum 2-FL concentration (g/l) | Yield (g 2-FL/g lactose) |
|---|---|---|---|---|---|
| BL21star(DE3) | pmBCGW + pHfucT2 | 2.56 ± 0.04 | 1.84 ± 0.05 | 0.01 ± 0.001 | 0.005 ± 0.001 |
| JM109(DE3) | pmBCGW + pHfucT2 | 2.55 ± 0.02 | 1.17 ± 0.05 | 0.14 ± 0.015 | 0.06 ± 0.005 |
|  |  | 14.54 ± 0.67 | 1.70 ± 0.28 | 1.23 ± 0.011 | 0.09 ± 0.004 |

BIOSYNTHESIS OF OLIGOSACCHARIDES

PRIORITY

This application claims the benefit of U.S. Ser. No. 61/740,118, filed on Dec. 20, 2012, which is incorporated herein in its entirety by reference.

BACKGROUND

Human milk oligosaccharides (HMOs) are known to be the most relevant factor for the development of intestinal microbiota in breast-fed infants [1]. Also, HMOs have been reported to play important roles in preventing adhesion of pathogens and toxins to epithelial surfaces [2]. Fucosyloligosaccharides, such as 2'-fucosyllactose, lacto-N-fucopentaose and lacto-N-difucohexaose, are common HMOs. Fucosylated oligosaccharides act as growth stimulating factors for select Bifidobacteria and soluble analogs of receptors for pathogenic bacteria, thereby protecting infants against infection from enteric pathogens and binding of toxins [3, 4]. Specifically, α-1,2-linked fucosylated oligosaccharides are reported to exhibit protective activity against several pathogens including *Campylobacter jejuni* [3, 5], *Salmonella enterica* serotype Typhimurium [6], Enterotoxigenic *E. coli* [7], *Helicobacter pylori* [8] and noroviruses [9]. Among them, 2'-fucosyllactose (2-FL) is typically the most abundant fucosyloligosaccharide in human milk and accounts for more than 30% of total HMOs [3, 5]. Low levels of 2-FL in the milk of some mothers have been reported to be associated with a higher rate of diarrhea in breast-fed infants [3]. Hence, 2-FL is a promising oligosaccharide for nutraceutical and pharmaceutical purposes.

SUMMARY OF THE INVENTION

The invention provides methods useful for producing 2'-fucosyllactose (2-FL) using a microbial system.

In one aspect the invention provides methods for producing 2'-fucosyllactose (2-FL) in a microorganism comprising i) providing a microorganism wherein the microorganism comprises a α-1,2 fucosyltransferase (FucT2) polynucleotide and a Guanosine 5'-diphospho-β-L-fucose (GDP-L-fucose) synthesis pathway; ii) fermenting the microorganism in the presence of lactose; and iii) collecting 2-FL from the microorganism or from a culture broth of the microorganism.

In particular embodiments the method further comprises purifying the 2-FL collected from the microorganism or from the culture broth of the microorganism by filtering through a purification column such as an activated charcoal and celite column.

In other particular embodiments the GDP-L-fucose synthesis pathway is modulated for enhanced GDP-L-fucose production. For example, the GDP-L-fucose synthesis pathway is modulated by at least one of amplification of GDP-D-mannose biosynthesis, regeneration of NADPH and manipulation of the guanosine nucleotides biosynthetic pathway.

In other particular embodiments, the microorganism is *Escherichia coli* or *Saccharomyces cerevisiae*. Suitable strains of *Escherichia coli* include the DH5α strain or JM strain. In other embodiments the microorganism has weak β-galactosidase activity. In yet other particular embodiments the JM strain *Escherichia coli* overexpresses at least one of a phosphomannomutase (Man B) polynucleotide, a mannose 1-phosphate guanylytransferase (Man C) polynucleotide, a GDP-D-mannose-4,6-dehydratse (Gmd) polynucleotide and a GDP-4-keto-6-deoxymannose 3,5-epimerase 4-reductase (WcaG) polynucleotide.

In other particular embodiments the α-1,2 fucosyltransferase polynucleotide is a *Helicobacter pylon, Caenorhabditis elegans, Rattus norvegicus, Mus musculus*, or *Homo sapien* polynucleotide.

In other embodiments the presence of lactose is at a concentration of between 0.5 g/l to 15 g/l. In yet other embodiments the lactose is converted into the 2'-fucosyllactose (2-FL) at a rate of greater than about 0.01, 0.05, 0.1, 0.2, 0.3, 0.4, 0.5, 0.6, 0.7, 0.8, 0.85 or more grams of 2-FL per gram of lactose.

In another aspect the invention provides a composition comprising a recombinant microorganism wherein the microorganism comprises a modulated GDP-L-fucose biosynthetic pathway and a α-1,2 fucosyltransferase polynucleotide.

BRIEF DESCRIPTION OF THE DRAWINGS

FIG. 6 shows the plasmids and primers used in the Examples.

FIG. 7 shows the results of the batch fermentations of Example 6.

DETAILED DESCRIPTION OF THE INVENTION

This invention provides a new biosynthesis method for production of 2-FL oligosaccharides using a microbial system. In particular a method for producing 2'-fucosyllactose (2-FL) in a microorganism, e.g., a bacterium or yeast, comprising i) providing a microorganism wherein the microorganism comprises a α-1,2 fucosyltransferase (FucT2) polynucleotide (e.g., a recombinant or heterologous polynucleotide) and a Guanosine 5'-diphospho-β-L-fucose (GDP-L-fucose) synthesis pathway ii) culturing the microorganism in the presence of lactose; and iii) collecting 2-FL from the microorganism or from a culture broth of the microorganism is provided.

Figure 1:
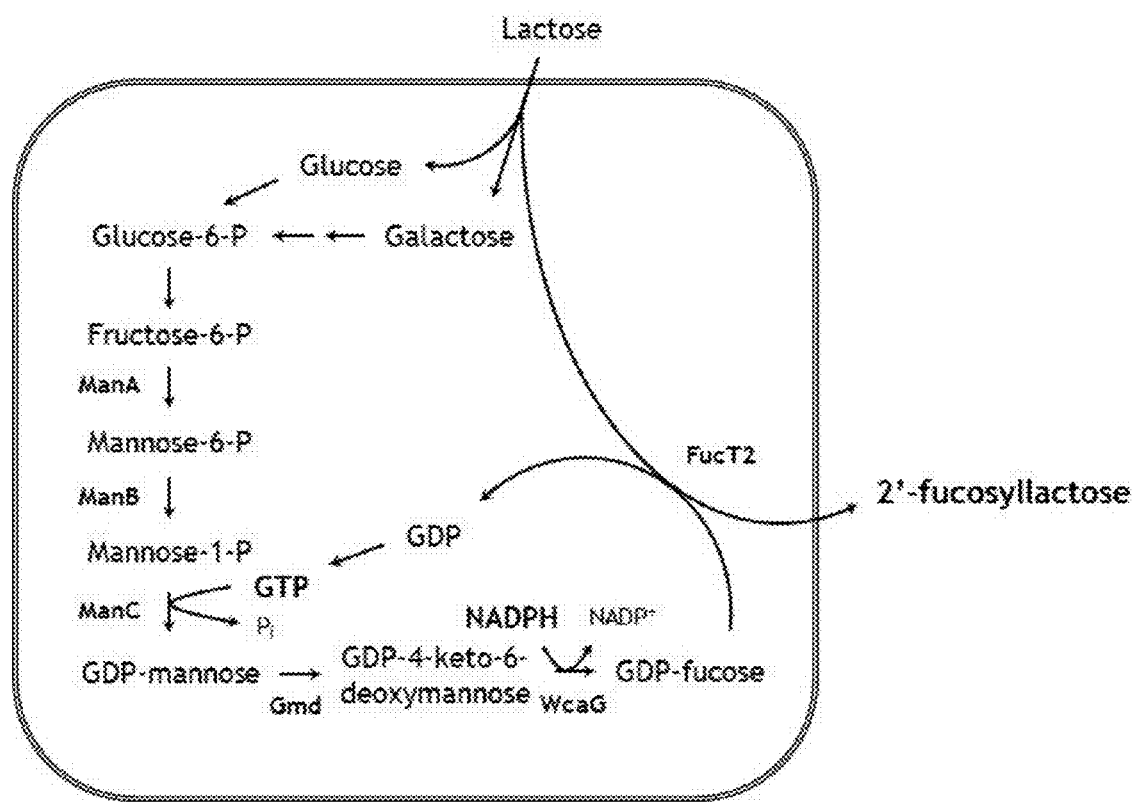
FIG. 1 illustrates an embodiment of the metabolic pathway for GDP-fucose and 2'-fucosyllactose (2-FL) biosynthesis in recombinant *E. coli*. The names of enzymes are abbreviated as follows; ManA, mannose 6-phosphate isomerase; ManB, phosphomannomutase; ManC, mannose 1-phosphate guanylyltransferase; Gmd, GDP-D-mannose-4,6-dehydratase; WcaG, GDP-4-keto-6-deoxymannose 3,5-epimerase 4-reductase; FucT2, α-1,2-fucosyltransferase. Pi, GDP and GTP denote phosphate, guanosine 5'-diphosphate and guanosine 5'-triphosphate.

2-FL can be synthesized through the enzymatic fucosylation of lactose by α-1,2 fucosyltransferase (FucT2), which requires guanosine 5'-diphosphate (GDP)-L-fucose as a donor of L-fucose [10]. *Escherichia coli* is known to be able to synthesize GDP-L-fucose since GDP-L-fucose is used for biosynthesis of colanic acid, one of the main components of the cell wall [11]. Therefore, 2-FL can be produced via engineering of the endogenous GDP-L-fucose biosynthetic pathway and expression or overexpression of the fucosyltransferase polynucleotide in metabolically engineered bacteria such as *E. coli* or yeast. FIG. 1 shows the metabolic pathway for biosynthesis of GDP-L-fucose and 2-FL in recombinant *E. coli*. Additionally, yeasts such as *Saccharomyces cerevisiae*, can be used to produce 2-FL in a similar manner as described for bacteria. *S. cerevisiae* makes GDP-mannose for cell wall purposes. Consequently, production of GDP-fucose in *S. cerevisae* requires heterologous expression of the last two steps in the GDP-fucose biosynthesis pathway depicted in FIG. 1.

Enzymatic biosynthesis of fucosyloligosaccharides using a recombinant microorganism and fucosyltransferase has been reported. Specifically, the enzymatic synthesis of 2-FL was examined by using purified FucT2, GDP-L-fucose and lactose [10], however, the high cost of GDP-L-fucose and FucT2 purification is a limiting factor for large-scale production of fucosyloligosaccharides. Production of several fucose-containing lacto-oligosaccharides in recombinant *E. coli* was also reported through simultaneous overexpression of fucosyltransferase and the regulatory protein for colanic acid biosynthesis [12, 13]. As biosynthesis of GDP-L-fucose, a key compound for biosynthesis of α-1,2-fucosylated oligosaccharides, requires a number of enzymes and cofactors such as NADPH and GTP, a whole-cell conversion approach is more realistic for industrial production than other chemical or enzymatic approaches [25].

A recombinant *E. coli* system for efficient production of GDP-L-fucose by metabolic engineering was previously developed through modulation of the GDP-L-fucose synthesis pathway. An enhancement of GDP-L-fucose production was achieved by modulation of several factors for biosynthesis of GDP-L-fucose such as amplification of GDP-D-mannose biosynthesis, regeneration of NADPH and manipulation of the guanosine nucleotides biosynthetic pathway [17-19]. Additionally, GDP-L-fucose production can be maximized through optimization of fermentation conditions.

GDP-L-fucose production can be amplified, increased or modulated in bacteria and yeast by, for example, providing expression or overexpression of one or more of ManA, ManB, ManC, Gmd, WcaG polynucleotides by any method known in the art (e.g., providing a recombinant polynucleotide to an organism for expression of one or more polypeptides, providing a promoter that provides for greater expression of one or more polynucleotides, optimizing culture conditions, and any other methods)

Figure 9:
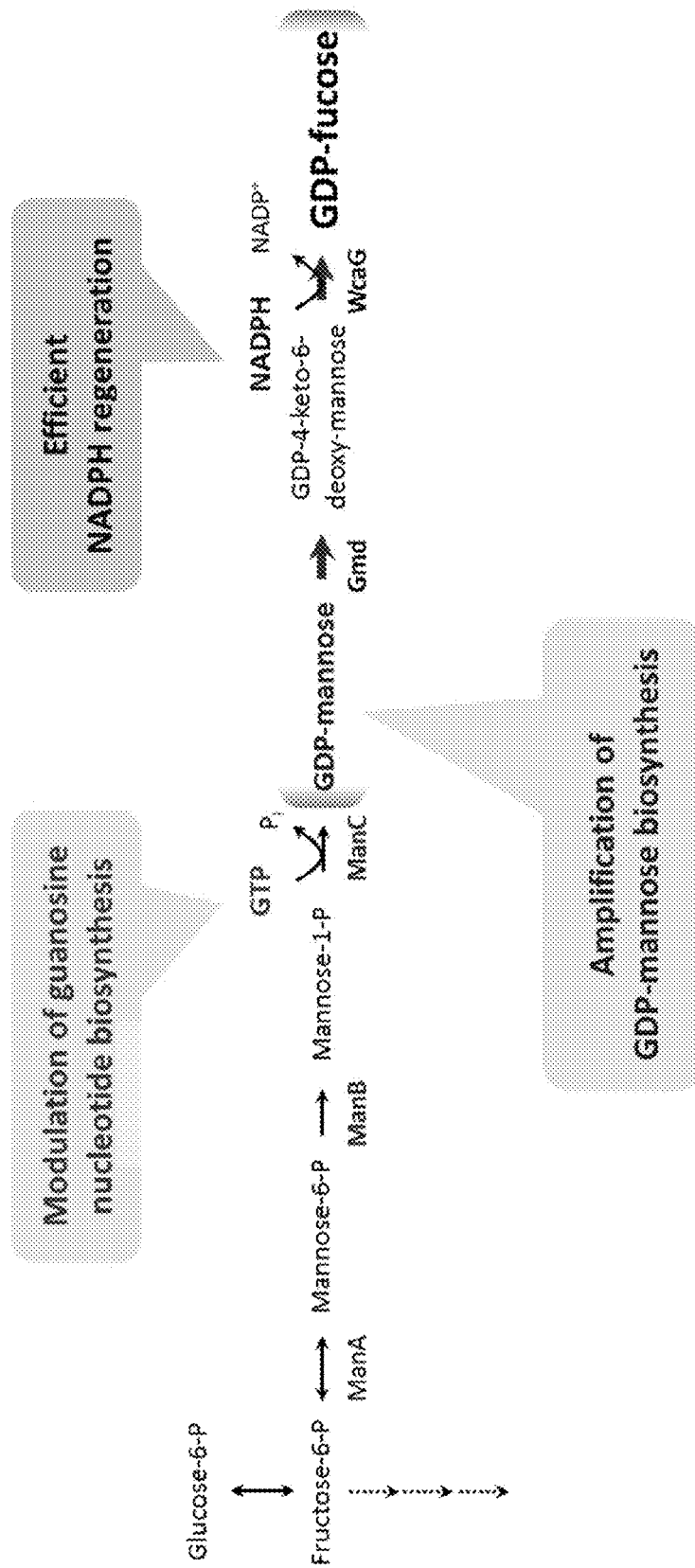
FIG. 9 illustrates the metabolic pathway for GDP-L-fucose biosynthesis. The names of enzymes are abbreviated as follows; ManA, mannose 6-phosphate isomerase; ManB, phosphomannomutase; ManC, mannose 1-phosphate guanylyltransferase; Gmd, GDP-D-mannose-4,6-dehydratase; WcaG, GDP-4-keto-6-deoxymannose 3,5-epimerase 4-reductase; Pi, GDP and GTP denote guanosine 5'-triphosphate. NADPH and NADP$^+$ denote nicotinamide adenine dinucleotide phosphate-oxidase and nicotinamide adenine dinucleotide phosphate.

The term "GDP-L-fucose synthesis pathway" as used herein refers to the metabolic pathway for GDP-L-fucose biosynthesis as illustrated in FIG. 9.

Amplification of GDP-D-mannose biosynthesis can be achieved by expression or overexpression of the polynucleotides involved in the biosynthesis of GDP-D-mannose such as phosphomannomutase (Man B) and mannose 1-phosphate guanylytransferase (Man C). Examples of methods for increasing GDP-D-mannose are disclosed in [18], which is incorporated by reference herein in its entirety. Regeneration of NADPH can be achieved by overexpression of a NADPH regenerating enzyme such as glucose-6-phophate dehydrogenase, isocitrate dehydrogenase, and NADP$^+$ in a recombinant microorganism. The particular methods for achieving regeneration of NADPH are disclosed in [17], which is incorporated by reference herein in its entirety. Manipulation of the guanosine nucleotides biosynthetic pathway can be achieved by increasing the intracellular levels of guanosine nucleotides and metabolic enzymes including inosine 5' monophosphate dehydrogenase, guasnosine 5'monophosphate synthetase, GMP reductase and guanosine-inosine kinase in a recombinant microorganism. The particular methods for achieving regeneration of NADPH are disclosed in [19], which is incorporated by reference herein in its entirety.

Each of these polynucleotides (e.g., those encoding ManA, ManB, ManC, Gmd, WcaG, glucose-6-phophate dehydrogenase, isocitrate dehydrogenase, NADP$^+$, inosine 5' monophosphate dehydrogenase, guasnosine 5'monophosphate synthetase, GMP reductase and guanosine-inosine kinase can be heterologous (e.g., from a different organism or species than that of the host cell) and can be present in a microbe of the invention alone or in combination with one or more of these polynucleotides).

The term "modulation" or "modulated" as used herein refers to a change, e.g., an increase or decrease, of a cell associated activity as compared to cell associated activity in the absence of the modulation methods.

The term "enhancement" or "enhanced" as used herein refers to increasing the activity or concentration of GDP-L-fucose product molecules.

In the present invention, a GDP-L-fucose production system is applied for efficient production of 2-FL by introduction of a FucT2 polynucleotide into a recombinant microorganism able to produce or overproduce GDP-L- fucose. Suitable FucT2 polynucleotides for use in the invention can be obtained from many organisms including, for example, from *Helicobacter pylori, Caenorhabditis elegans, Rattus norvegicus, Mus musculus,* or *Homo sapien.*

In particular embodiments the production of GDP-L-fucose is modulated by a recombinant microorganism that expresses or overexpresses enzymes that are essential for GDP-fucose biosynthesis such as GDP-D-mannose-4,6-dehydratse (Gmd) and GDP-4-keto-6-deoxymannose 3,5-epimerase 4-reductase (WcaG). Additionally, the recombinant microorganism can be modulated to express or overexpress enzymes involved in the biosynthesis of GDP-D-mannose. For example, the recombinant microorganism can be constructed for the combinational overexpression of enzymes such as phosphomannomutase (Man B) and mannose 1-phosphate guanylytransferase (Man C). The overexpression of the enzymes can be achieved by constructing inducible overexpression vectors encoding for the desired enzyme. The particular methods for producing recombinant microorganisms that overexpress GMD, WcaG, Man B and Man C are disclosed in [18], which is incorporated by reference herein in its entirety. Suitable recombinant microorganisms include but are not limited to bacteria such as *E. coli* and yeast such as *S. cerevisiae.*

The term "overexpression" or "overexpressed" as used herein refers to a level of enzyme or polypeptide expression that is greater than what is measured in a wild-type cell of the same species as the host cell that has not been genetically altered.

The methods of the invention provide for the production of 2-FL in the amount of 0.01 g/L to 4.35 g/L. For example, 2-FL is produced using a recombinant or mutant microorganism that overexpresses FucT2 (e.g., 0.01 g/L of 2-FL produced). Additionally, 2-FL is produced from a recombinant or mutant microorganism that is optimized for 2-FL production because it uses just enough lactose to achieve growth, and conserves most lactose for use in making 2-FL (e.g., 0.15 g/L of 2-FL produced). Moreover, 2-FL is produced by culturing a microorganism expressing or overexpressing FucT2 and has a modulated or amplified GDP-L-fucose biosynthetic pathway under optimized batch fermentation conditions (e.g., 1.23 g/L of 2-FL) or under fed-batch fermentation conditions (e.g., 4.35 g/L of 2-FL produced). Therefore, 2-FL can be produced at about 0.005, 0.01, 0.05, 0.1, 0.5, 1.0, 1.5, 2.0, 2.5, 3.0, 3.5, 4.0, 4.5, 5.0 or more g/L.

Optimized fermentation conditions, such as batch fermentation conditions include regulation of the culture temperature and the lactose concentration. For example, the culture can be maintained at a temperature wherein the substrate is efficiently used and 2-FL is maximally produced with minimal acetate production. Specifically, the culture temperature is maintained between about 25° C. and about 37° C. with the optimal temperature being about 25° C. Additionally, under optimal conditions the lactose substrate concentration is between 0.5 g/L to 50 g/L. In particular embodiments the lactose is added at a concentration of about 0.5 g/L, 10 g/L, 20 g/L, 30 g/L, 40 g/L, 50 g/L or more. In other embodiments 2-FL production is performed using fed-batch fermentation wherein lactose is continuously supplied throughout the fermentation process at a concentration of about 5, 10, 15, 20, 25, 30, 35, 40 or more g/L.

Expression or overexpression of the amplified or modulated GDP-L-fucose pathway in combination with a FucT2 polynucleotide provides a system wherein 2-FL is synthesized within one cell. Whole cell biosynthesis of 2-FL from lactose can be assessed in a series of batch fermentations for recombinant microbes expressing or overexpressing the necessary genes for GDP-L-fucose overproduction and FucT2. An EFM analysis for 2-FL production in the recombinant *E. coli* can also be used to compare and evaluate experimental results. See Appendix. To construct an efficient 2-FL production system by metabolic engineering, an understanding and detailed analysis of a cellular metabolic network involved in the 2-FL biosynthesis is important. Elementary flux mode (EFM) analysis has emerged as a powerful tool for metabolic pathway analysis. EFM analysis is a useful mathematical tool for defining and describing all metabolic routes that are both stoichiometrically and thermodynamically feasible for a group of enzymes. The EFM analysis can decompose a complex metabolic network of many highly interconnected reactions into uniquely organized pathways that support steady state of metabolism. EFM analysis can provide identification of all genetically independent pathways, determination of the most efficient physiological state of a cell, and analysis of metabolic network properties such as robustness and regulation [14-16]. Hence, it can be a useful tool for understanding dynamics of cellular metabolism and rational design of the host strain's metabolism for 2-FL production.

In one aspect, a method of the invention includes, fermenting the recombinant microorganism overexpressing the GDP-L-fucose polynucleotides (e.g., one or more of polynucleotides capable of expressing ManA, ManB, ManC, Gmd, WcaG, glucose-6-phophate dehydrogenase, isocitrate dehydrogenase, $NADP^+$, inosine 5' monophosphate dehydrogenase, guasnosine 5'monophosphate synthetase, GMP reductase and guanosine-inosine kinase) and a FucT2 polynucleotide in the presence of a lactose substrate. The use of lactose as a substrate for the methods described herein is advantageous over previous methods using glucose because it allows for the production of 2-FL by a whole-cell conversion approach rather than a chemical or enzymatic approach. The whole-cell conversion approach provides for efficient production of 2-FL directly without the need for any costly starting materials such as purified GDP-L-fucose. Instead, the whole-cell approach derives all the necessary materials for the production of the 2-FL directly from the recombinant microorganism. Due to catabolite repression, lactose transport is repressed when glucose is used as a substrate. Thus, 2-FL production using glucose cannot be achieved using a whole-cell conversion approach because GDP-L-fucose must first be produced in a cell and then enzymatically added to lactose.

In one embodiment of the invention the culture medium has less than about 20, 10, 5, 4, 3, 2, 1 or less g/L of glucose.

The microorganism used in the methods described herein can be unable to assimilate lactose or to utilize lactose extremely inefficiently due to, for example, a partial deletion or inactivation of one or more lacZ genes, which code for β-galactosidase such that the microorganism produces 20, 30, 40, 50, 60, 70, 80, 90, 95, 99% or less β-galactosidase than a microorganism with a non-defective lacZ gene. In particular embodiments the microorganism has weak β-galactosidase activity as compared to a microorganism that has a non-defective lacZ gene. The term "weak β-galactosidase activity" as used herein refers to a cell that has residual β-galactosidase activity which provides the cell only enough lactose to survive on.

Examples of suitable microorganisms include *S. cerevisiae* and *E. coli* strains, such as DH5α and JM series. In one embodiment the microorganism is a slow-lactose utilization microorganism wherein it uses just enough lactose to achieve growth, and conserves most lactose for use in making 2-FL. Several attempts for production of fucosylated (or sialylated) oligosaccharides from lactose have been made using the derivative of *E. coli* JM107 and JM109 since these strains are unable to produce an active β-galactosidase due to the insertion of the M15 single strand DNA into the lacZ gene [12, 13, 26, 27]. In these cases, glucose (or glycerol) was used as another carbon source for GDP-fucose production (or CMP-N-acetylneuraminic acid). These nucleotide sugars are subsequently used for fucosylation (or sialylation).

Surprisingly, it was determined that microorganisms that produce less β-galactosidase than a microorganism with a non-defective lacZ gene are the best producers of 2-FL (as compared to microorganisms that express normal levels of β-galactosidase or express no β-galactosidase) using the methods of the invention. *E. coli* JM109 (DE3) was chosen as an example of a suitable host strain for 2-FL production.

In one aspect, a method of the invention includes collecting 2-FL from the microorganism or from a culture broth of the microorganism. Following collection, the 2-FL is purified using a purification columns such as an activated charcoal and celite column.

Polynucleotides

Polynucleotides contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides.

Polynucleotides can be isolated from nucleic acid sequences present in, for example, a bacterial or yeast culture. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector, but any kind of vector can be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide. Polynucleotides of the invention can be present in an expression vector, which can be present in a host cell.

Polynucleotides can encode full-length polypeptides, polypeptide fragments, and variant or fusion polypeptides. A polynucleotide encodes a polypeptide, which can be an enzyme that has biological activity.

A polypeptide expressed by a polynucleotide of the invention reacts substantially the same as a wild-type polypeptide in an assay of biological activity, e.g. has 80-120% of the activity of the wild-type polypeptide. A wild-type polypeptide is a polypeptide that is not genetically altered and that has an average biological activity in a natural population of the organism from which it is derived.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used.

Unless otherwise explained, all technical and scientific terms used herein have the same meaning as commonly understood by one of ordinary skill in the art to which a disclosed disclosure belongs.

The singular terms "a," "an," and "the" include plural referents unless context clearly indicates otherwise. Similarly, the word "or" is intended to include "and" unless the context clearly indicates otherwise.

The disclosure may be further understood by the following non-limiting examples. Although the description herein contains many specificities, these should not be construed as limiting the scope of the disclosure but as merely providing illustrations of some of the presently preferred embodiments of the disclosure. For example, thus the scope of the disclosure should be determined by the appended aspects and their equivalents, rather than by the examples given.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

EXAMPLES

Example 1: Strains and Plasmids

E. coli TOP10 [F− mcrA Δ(mrr-hsdRMS-mcrBC) φ80lacZΔM15 ΔlacX74 recA1 araD139 Δ(ara-leu) 7697 galU galK rpsL (Str$^R$) endA1 nupG] was used for genetic manipulation. E. coli BL21star (DE3) [F−, ompT, hsdSB($r_B^-$ $m_B^-$), gal, dcm me131 (DE3)] (Invitrogen, Carlsbad, Calif., USA) and JM109 (DE3) [endA1 glnV44 thi-1 relA1 gyrA96 recA1 mcrB+ Δ(lac-proAB) e14− [F' traD36 proAB+ lacI$^q$ lacZΔM15] hsdR17($r_K^-$$m_K^+$) (DE3)] (NEB, Ipswich, Mass., USA) were used for production of GDP-L-fucose and 2-FL. Plasmid pmBCGW containing the polycistronic gmd-wcaG gene cluster and manB-manC gene cluster was previously constructed using plasmid pETDuet-1 [18]. The gene encoding FucT2 was obtained by the polymerase chain reactions (PCR) using the genomic DNA of the Helicobacter pylori 26695 strain (ATCC 700392) as template [20]. Two PCR primers of fucT2_F and fucT2_R were used for the amplification of the FucT2 gene. After digestion of PCR fragments of the FucT2 gene and pCOLADuet-1 (Merck Biosciences, Darmstadt, Germany) with NcoI and SacI, the DNA fragments were ligated to construct plasmid pHfucT2. Plasmids and primers used in this work are shown in FIG. 6. The constructed plasmid was confirmed by DNA sequencing. The conditions for PCR reaction, DNA manipulation and bacterial transformation followed the descriptions in [21].

Example 2: Batch Fermentation

Batch fermentation was carried out in a 250 ml flask containing 50 ml of LB medium at 25° C. and pH 6.8. Agitation speed was maintained at 250 rpm. When dry cell mass reached 0.3 g/l, 0.1 mM isopropyl-β-D-thiogalactopyranoside (IPTG) was added to culture broth. After 3 h of additional cultivation, 2.6 g/l (or 14.5 g/l) lactose was added for 2-FL production.

Example 3: Analytical Methods

Cell concentration was measured by optical density (OD) at 600 nm using a spectrophotometer (Biomate 5, Thermo, N.Y., USA). Overexpression of FucT2 inside the cell was analyzed by using sodium dodecyl sulfate-polyacrylamide gel electrophoresis (SDS-PAGE, 12% polyacrylamide). After 3 h of 0.1 mM IPTG induction, cells were collected and the concentration was adjusted to around 7.2 g/l. They were resuspended in 50 mM potassium phosphate buffer (pH 7.0) and disrupted by an ultrasonic processor. After centrifugation at 15,000×g for 20 min, the supernatant (soluble fraction) and debris (insoluble fraction) were separated. Ten microliters of the soluble protein fraction (approximately 0.04 mg) and the same volume of the total and insoluble protein fractions were subjected to SDS-PAGE. Gels were stained with Coomassie brilliant blue solution and images were analyzed using a densitometer.

Concentrations of lactose, 2-FL and acetate in batch fermentations were determined by using a high performance liquid chromatography (HPLC) system (Agilent Technologies 1200 Series) equipped with a Rezex ROA Organic Acid H+ column (Phenomenex, Torrance, Calif., USA) and a refractive index (RI) detector (Agilent, Palo Alto, Calif., USA). The column was eluted with 0.01N $H_2SO_4$ at a flow rate of 0.6 ml/min at 50° C.

In order to confirm 2-FL biosynthesis, culture broth at the end of the batch fermentation was collected and analyzed using a liquid chromatography/mass spectrometry (LC/MS) system. The LC (Agilent Technologies 1100 Series) was equipped with an Agilent Zorbax Eclipse ZDB-C8 (4.6×150 mm, 5 micron) column and an Agilent LC/MSD Trap XCT Plus detector. The column was eluted at a flow rate of 0.4 ml/min by the following gradient program: 95% (v/v) eluent A (15 mM ammonium acetate) and 5% eluent B (acetonitrile) for 1 min; 5% to 95% eluent B over 6 min; 95% eluent B over 10 min. The scan range for MS was 70-600 mass-to-charge ratio (m/z).

Example 4: Construction of Metabolic Network Model for E. coli Producing 2-FL from Lactose A metabolic network model was constructed for 2-FL producing E. coli that grows on lactose. The E. coli network was based on a model that was introduced by Stelling et al. [22] to examine the relationship between structure and function in metabolic networks. Furthermore, the model has been used for calculating elementary flux modes in previous reports [23, 24]. The metabolic network was composed of 108 reactions, which were involved in carbon central metabolism, amino acid synthesis, fatty acid synthesis and biomass production (Supplementary information: META-TOOL input file). The catabolic part of the model included substrate uptake reactions, glycolysis, pentose phosphate pathway, TCA cycle, and excretion of by-products (e.g. acetate, formate, lactate, and ethanol). Previous networks were extended to include the anaplerotic reactions (e.g. malic enzyme and pyruvate oxidase) in addition to parallel pathways for initial acetate metabolism. The anabolic part of the model covers the conversion of precursors into building blocks like macromolecules and biomass. The core E. coli model from Stelling et al. [22] was modified in this research to account for lactose consumption and synthesis of 2-FL. Among the reactions added for 2-FL synthesis, some minor adjustments were made to simplify the model. Lactose was assumed to break down to 2 moles of glucose because galactose can be easily converted into glucose-6-phosphate. ATP was used in place of GTP for energy transfer. As for the mass balance, it should be noted that ADP is formed whenever ATP is consumed for all the metabolic reactions in the network. The mass balance equation on ATP is therefore the negative of the mass balance on ADP and thus the two equations are linearly dependent. Therefore, ADP can be excluded from the model in order to simplify the subsequent EFM calculation. The same is true for other cofactor pairs like NADP/NADPH and NAD/NADH. The EFM pathways in the model were estimated using METATOOL 5.1 [14, 16] with Matlab.

Figure 2:
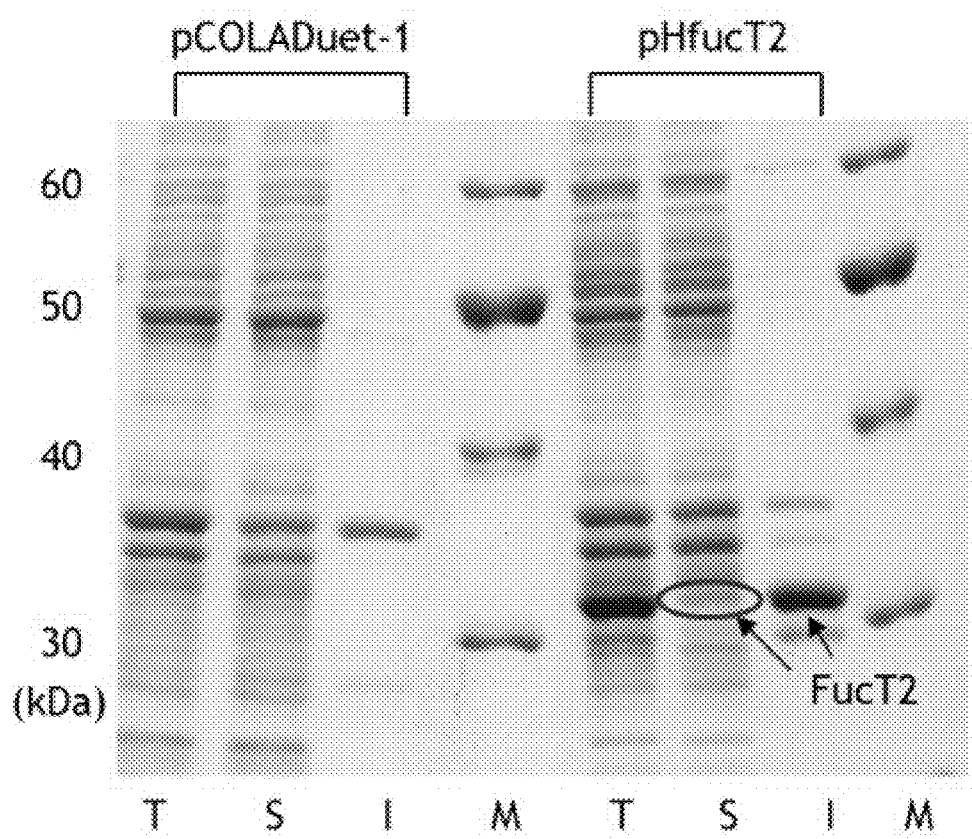
FIG. 2 illustrates an embodiment of SDS-PAGE analysis of the cell crude extract of recombinant *E. coli* BL21star (DE3) strains harboring pCOLADuet-1 and pHfucT2, respectively. Cells were harvested after 3 h of 0.1 mM IPTG induction. T, S and I denote total, soluble and insoluble protein fractions, respectively. The arrow indicates the corresponding protein band with the estimated molecular weight of FucT2. Lane M indicates size marker.

Example 5: Expression of α-1,2-Fucosyltransferase (FucT2) in Recombinant E. coli The expression pattern of FucT2 was investigated during a batch fermentation of recombinant E. coli harboring plasmid pHfucT2. The FucT2 polynucleotide from H. pylori was cloned and overexpressed in the E. coli BL21star (DE3) strain. In order to maximize the expression of the soluble form of FucT2 in the recombinant *E. coli*, 0.1 mM of IPTG was used. As shown in FIG. 2, a 33 kDa protein (consistent with FucT2, [20]) was found in both soluble and insoluble fraction. While a significant amount of FucT2 was expressed in inclusion bodies, biosynthesis of 2-FL was expected because a soluble form of FucT2 was available as well.

Example 6: Batch Fermentations

From the preliminary experiments (whole cell bioconversion of 2 g/l lactose with *E. coli* BL21star (DE3) strain), it was concluded that the *E. coli* BL21star (DE3) strain was not beneficial for 2-FL production because it consumed lactose for growth and maintenance instead of converting to 2-FL (data not shown). Most of the initially added lactose was consumed within 12 h of fermentation with a marginal growth during the fermentation (data not shown). Some *E. coli* strains, such as DH5α and JM series, are known to be unable to assimilate lactose or utilize lactose extremely inefficiently due to partial deletion of the lacZ gene, which codes for β-galactosidase. As such, these *E. coli* strains are useful for 2-FL production. Hence, *E. coli* JM109 (DE3) enabling overexpressing proteins under the control of T7 promoter was used as an alternative host stain for 2-FL production.

Figure 3:
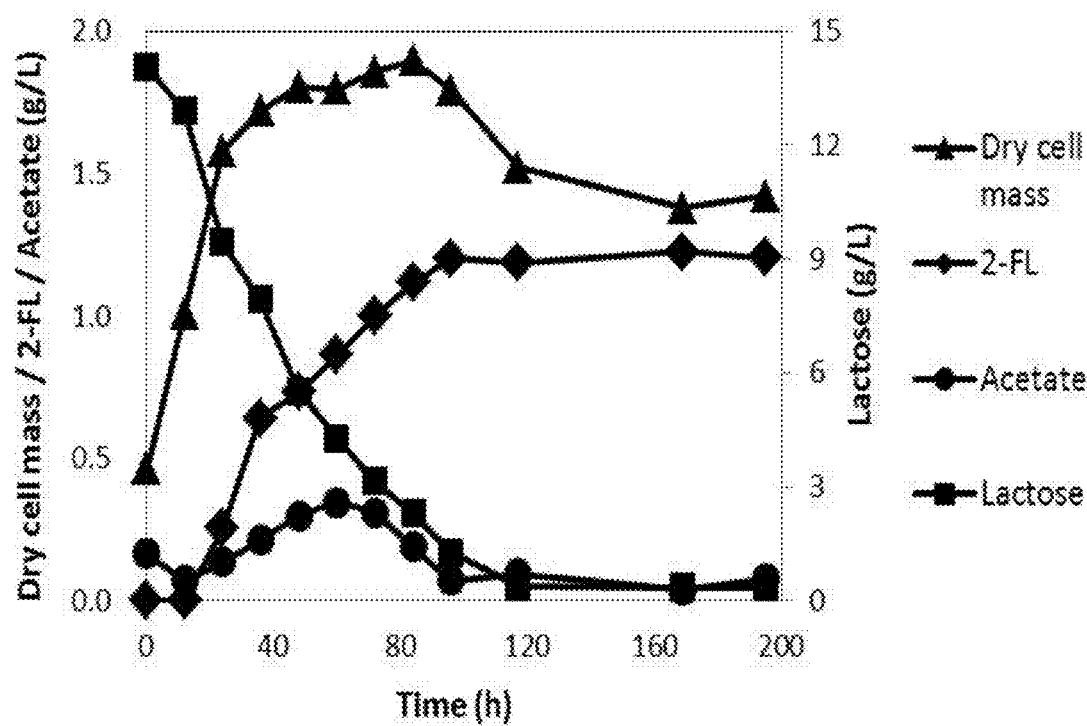
FIG. 3 illustrates an embodiment of a profile of 2-FL production in the batch fermentation of recombinant *E. coli* JM109 (DE3) strain harboring plasmids pmBCGW and pHfucT2. After 3 h of 0.1 mM IPTG induction, 14.5 g/l of lactose was added for 2-FL production. Symbols denote as follows; triangle, dry cell mass; diamond, 2-FL concentration; square, lactose concentration; circle, acetate concentration. Measurement of cell, lactose, acetate and 2-FL concentrations were done by three independent experiments. Symbols in the figure show the representative values of the batch fermentations.

2-FL production for BL21star (DE3) and JM109 (DE3) was compared under batch fermentation conditions. In order to allow sufficient production of both GDP-L-fucose biosynthetic enzymes and FucT2 inside the cells, the cells were cultivated for 3 hours after 0.1 mM IPTG induction. Then, 2.6 g/l of lactose was added to initiate 2-FL production without addition of additional sugar because GDP-L-fucose can be produced from LB media [17, 18]. During the fermentations, extracellular 2-FL production (in the medium) was monitored by HPLC analysis. As a result, a small amount of 2-FL (10 mg/l) was produced in the batch fermentation of recombinant *E. coli* BL21star (DE3). Meanwhile, much higher amount of 2-FL was produced in the batch fermentation of recombinant *E. coli* JM109 (DE3). About 140 mg/l of 2-FL was produced from 2.6 g/l of lactose while 0.4 g/l of lactose remained unused at the end of the fermentation (data not shown). These results indicate that the lactose concentration should be controlled at more than 0.5 g/l to maintain 2-FL production. Consequently, a yield of 60 mg 2-FL/g lactose was obtained from the batch fermentation of *E. coli* JM109 (DE3) when 2.6 g/l of lactose was used. In order to obtain a higher amount of 2-FL, a batch fermentation with a higher concentration of lactose was carried out. FIG. 3 shows the profiles of lactose consumption and 2-FL production in the batch fermentation of recombinant *E. coli* JM109 (DE3) with 14.5 g/l lactose. The cells consumed lactose slowly but produced 2-FL constantly for 96 hours. After 96 h of fermentation, the 2-FL concentration did not increase any further and lactose consumption stopped. As a result, a maximum 2-FL concentration of 1.23 g/l was obtained, which corresponded to a nine-fold (1.23 g/l vs. 140 mg/l) increase as compared with the previous fermentation with 2.6 g/l lactose. 2-FL yield increased to 90 mg 2-FL/g lactose when 14.5 g/l of lactose was used. The results of the batch fermentations are shown in FIG. 7.

It is generally known that acetate formation is accelerated when the metabolic fluxes to pyruvate exceed the capacity of the respiratory metabolism [28, 29]. Slow consumption of lactose might not lead to acetate formation, suggesting that the lactose utilization rate by *E. coli* JM109 (DE3) is not fast enough to cause acetate formation.

Example 7: Confirmation of 2-FL Biosynthesis by Recombinant *E. coli* Overexpressing GDP-L-Fucose Biosynthetic Enzymes and FucT2

Figure 4:
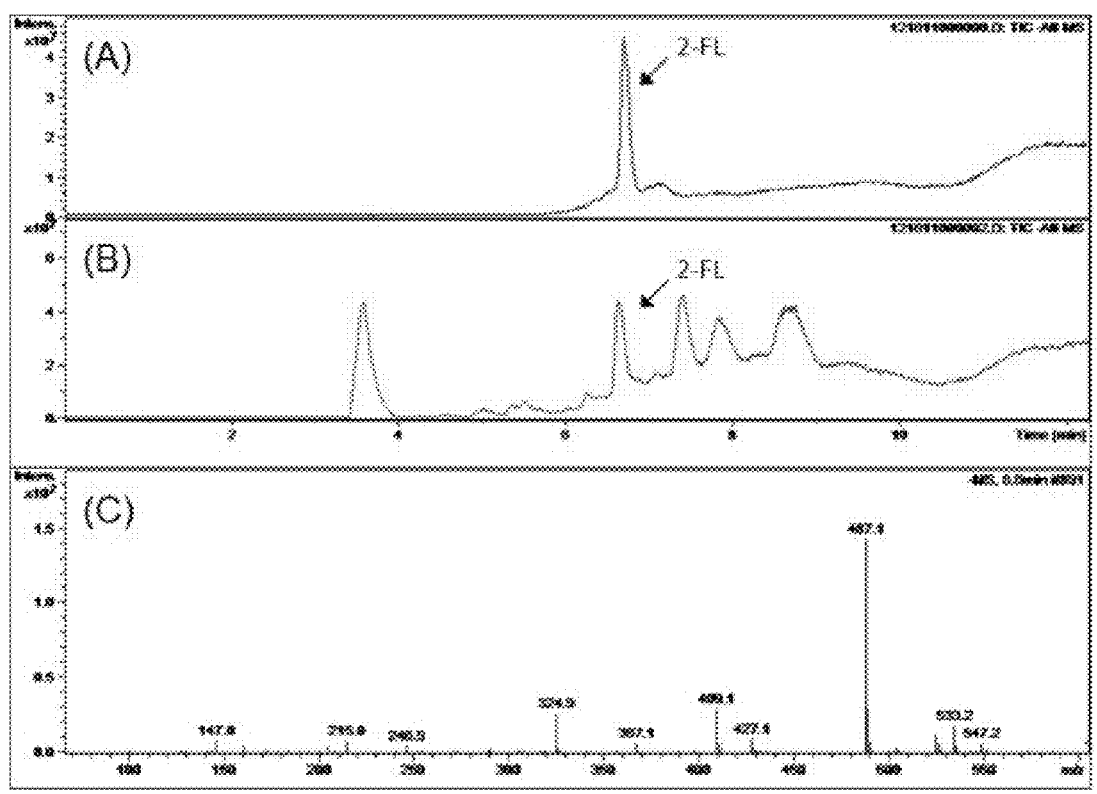
FIG. 4 illustrates an embodiment of LC/MS analysis of 2-FL biosynthesis in the batch fermentation of the recombinant *E. coli* JM109 (DE3) overexpressing ManB, ManC, Gmd, WcaG and FucT2. At the end of batch fermentation, culture broth was collected for confirmation of extracellular 2-FL production. HPLC analysis of 100 mg/l 2-FL standard solution (A), HPLC analysis of culture broth of *E. coli* JM109 (DE3) harboring pmBCGW+pHfucT2 (B) and MS analysis of the compound with the retention time=6.6 min in the culture broth of *E. coli* JM109 (DE3) harboring pmBCGW+pHfucT2 (C).

LC/MS analysis was performed to confirm the biosynthesis of 2-FL in the recombinant *E. coli* JM109 (DE3) strain overexpressing ManB, ManC, Gmd, WcaG and FucT2. HPLC data showed that a compound with the identical retention time to 2-FL was detected in the culture broth (FIG. 4B). MS scanning data (compound with RT=6.6 min) showed ion fragment of m/z 487.1, which is compatible with 2-FL (FIG. 4C).

Figure 5:
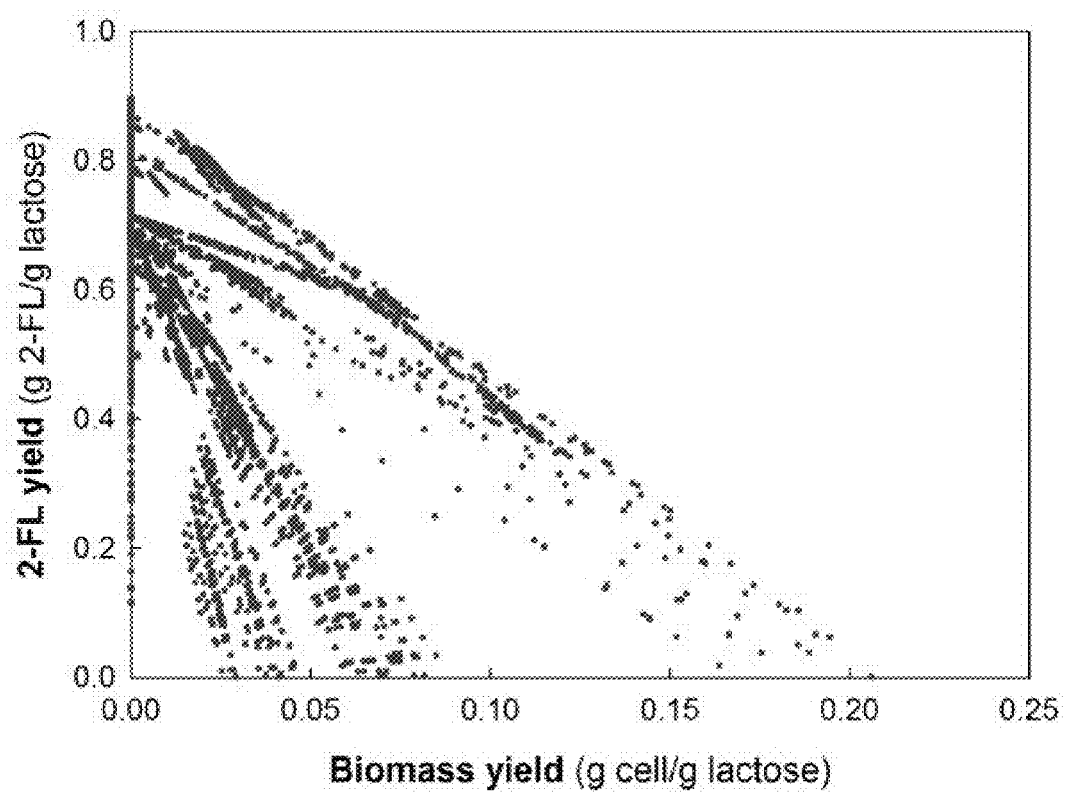
FIG. 5 illustrates an embodiment of a calculation of the theoretical maximum yield of 2-FL from lactose. Elementary flux mode (EFM) analysis was carried out for 2-FL producing *E. coli*.

Example 8: Evaluation of 2-FL Yield Using EFM Analysis for 2-FL Producing *E. coli* from Lactose In order to evaluate the efficiency of 2-FL production from lactose using the recombinant *E. coli* JM109 (DE3) strain, elementary flux mode (EFM) analysis was employed to estimate a maximum theoretical yield of 2-FL from lactose. FIG. 5 shows the prediction of theoretical 2-FL yield versus biomass yield for *E. coli* growing on lactose. The experimental result from a batch fermentation of 14.5 g/l of lactose resulted in a biomass yield of 0.1 g biomass/g lactose. This suggests that 2-FL production from lactose by the engineered *E. coli* reached 20% of the maximum 2-FL production capacity.

This result indicates that more than 90% of lactose consumed was used for other purposes such as biomass production and endogeneous metabolism. Slow consumption of lactose was also observed in the batch fermentation with mixed sugars (2 g/l of lactose and 5 g/l of mannose), where it was expected that lactose could be mainly used for 2-FL production as mannose might be used for cell growth. Although an enhancement of 2-FL yield (0.13 g 2-FL/g lactose) was obtained, most of the consumed lactose was not used for 2-FL production (data not shown).

Example 9: Purification of 2-FL

The 2-FL produced from lactose using the recombinant *E. coli* JM109 (DE3) strain was collected from the fermentation supernatant by filtering the supernatant through an activated charcoal and celite column. Specifically, the LB fermentation media was applied to the activated carbon celite filter (1:1) and washed with 5% ethanol. The 2-FL was then eluted with 30% ethanol and the ethanol was allowed to evaporate.

Chemical analysis using MS of the purified sample confirmed an ion fragment of 501.775 m/z, which is consistent with 2-FL.

Example 10: Large Scale Production of 2-FL

Figure 8:
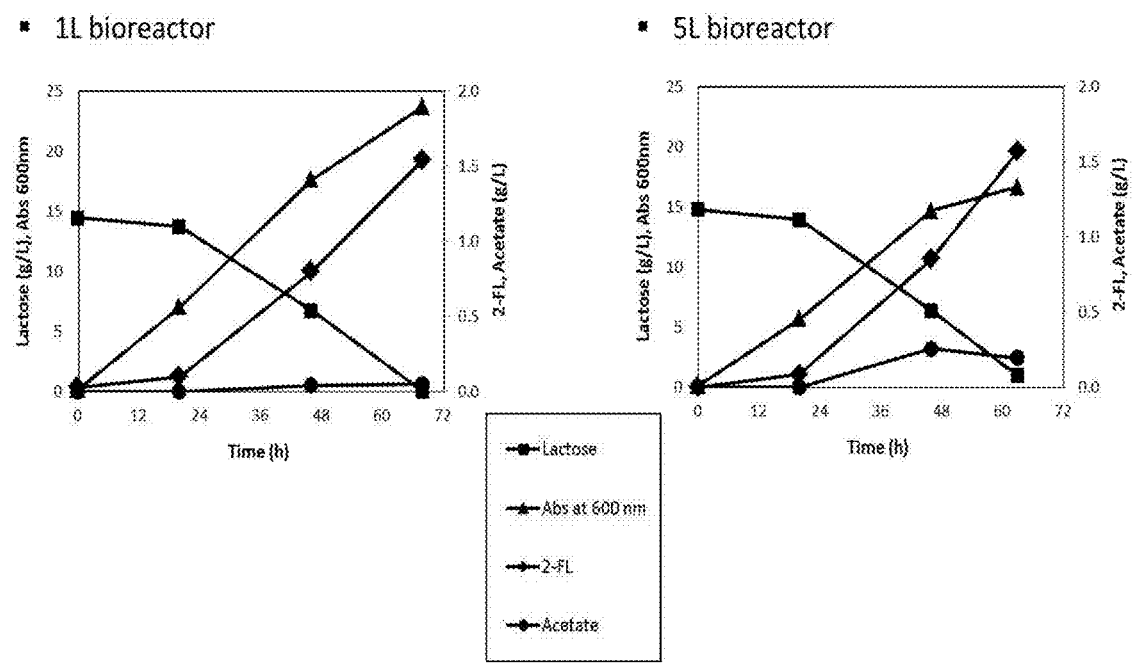
FIG. 8 illustrates an embodiment of a profile of large scale production of 2-FL in the batch fermentation of recombinant *E. coli* JM109 harboring plasmids pmBCGW and pHfucT2 using a 1 L and 5 L bioreactor. Symbols denote as follows; square, lactose; triangle, A600 nm; diamond, 2-FL concentration; circle, acetate concentration.

The methods of the invention were applied to a large scale production of 2-FL using a bioreactor. Specifically, recombinant JM109 (DE3) was fermented in a 1 L and 5 L bioreactor at a concentration of 15 g/L of lactose at 25° C. Under these conditions, the fermentation in the 1 L and 5 L reactors produced ~1.5 g/L. The results of the batch fermentations are shown in FIG. 8.

REFERENCES

1. Kunz C, Rudloff S: Health promoting aspects of milk oligosaccharides. *International Dairy Journal* 2006, 16(11):1341-1346.

2. Bode L: Recent advances on structure, metabolism, and function of human milk oligosaccharides. *Journal of Nutrition* 2006, 136(8):2127-2130.
3. Morrow A L, Ruiz-Palacios G M, Altaye M, Jiang X, Guerrero M L, Meinzen-Derr J K, Farkas T, Chaturvedi P, Pickering L K, Newburg D S: Human milk oligosaccharides are associated with protection against diarrhea in breast-fed infants. *Journal of Pediatrics* 2004, 145(3): 297-303.
4. Newburg D S, Ruiz-Palacios G M, Altaye M, Chaturvedi P, Meinzen-Derr J, Guerrero M D, Morrow A L: Innate protection conferred by fucosylated oligosaccharides of human milk against diarrhea in breastfed infants. *Glycobiology* 2004, 14(3):253-263.
5. Chaturvedi P, Warren C D, Altaye M, Morrow A L, Ruiz-Palacios G, Pickering L K, Newburg D S: Fucosylated human milk oligosaccharides vary between individuals and over the course of lactation. *Glycobiology* 2001, 11(5):365-372.
6. Chessa D, Winter M G, Jakomin M, Bäumler A J: *Salmonella enterica* serotype Typhimurium Std fimbriae bind terminal α(1,2)fucose residues in the cecal mucosa. *Molecular Microbiology* 2009, 71(4):864-875.
7. Newburg D S, Pickering L K, McCluer R H, Cleary T G: Fucosylated oligosaccharides of human milk protect suckling mice from heat-stabile enterotoxin of *Escherichia coli*. *Journal of Infectious Diseases* 1990, 162(5): 1075-1080.
8. Maqalhães A, Reis C A: *Helicobacter pylori* adhesion to gastric epithelial cells is mediated by glycan receptors. *Brazilian Journal of Medical and Biological Research* 2010, 43(7):611-618.
9. Newburg D S, Ruiz-Palacios G M, Morrow A L: Human milk glycans protect infants against enteric pathogens. *Annual Review of Nutrition* 2005, 25:37-58.
10. Albermann C, Piepersberg W, Wehmeier U F: Synthesis of the milk oligosaccharide 2'-fucosyllactose using recombinant bacterial enzymes. *Carbohydrate Research* 2001, 334(2):97-103.
11. Stevenson G, Andrianopoulos K, Hobbs M, Reeves P R: Organization of the *Escherichia coli* K-12 gene cluster responsible for production of the extracellular polysaccharide colanic acid. *Journal of Bacteriology* 1996, 178 (16):4885-4893.
12. Drouillard S, Driguez H, Samain E: Large scale synthesis of H antigen oligosaccharides by expressing *Helicobacter pylori* α1,2-fucosyltransferase in metabolically engineered *Escherichia coli* cells. *Angewandte Chemie* 2006, 118(11):1810-1812.
13. Dumon C, Priem B, Martin S L, Heyraud A, Bosso C, Samain E: In vivo fucosylation of lacto-N-neotetraose and lacto-N-neohexaose by heterologous expression of *Helicobacter pylori* α-1,3 fucosyltransferase in engineered *Escherichia coli*. *Glycoconjugate Journal* 2001, 18(6): 465-474.
14. Pfeiffer T, Sánchez-Valdenebro I, Nuño J C, Montero F, Schuster S: METATOOL: for studying metabolic networks. *Bioinfomatics* 1999, 15(3):251-257.
15. Schuster S, Fell D A, Dandekar T: A general definition of metabolic pathways useful for systematic organization and analysis of complex metabolic networks. *Nature Biotechnology* 2000, 18(3):326-332.
16. Trinh C T, Wlaschin A, Srienc F: Elementary mode analysis: a useful metabolic pathway analysis tool for characterizing cellular metabolism. *Applied Microbiology and Biotechnology* 2009, 81(5):813-826.
17. Lee W H, Chin Y W, Han N S, Kim M D, Seo J H. Enhanced production of GDP-L-fucose by overexpression of NADPH regenerator in recombinant *Escherichia coli*. *Applied Microbiology and Biotechnology* 2011, 91(4): 967-976.
18. Lee W H, Han N S, Park Y C, Seo J H: Modulation of guanosine 5'-diphosphate-D-mannose metabolism in recombinant *Escherichia coli* for production of guanosine 5'-diphosphate-L-fucose. *Bioresource Technology* 2009, 100(24):6143-6148.
19. Lee W H, Shin S Y, Kim M D, Han N S, Seo J H: Modulation of guanosine nucleotides biosynthetic pathways enhanced GDP-L-fucose production in recombinant *Escherichia coli*. *Applied Microbiology and Biotechnology* 2012, 93(6):2327-2334.
20. Wang G, Boulton P G, Chan N W, Palcic M M, Taylor D E: Novel *Helicobacter pylori* α1,2-fucosyltransferase, a key enzyme in the synthesis of Lewis antigens. *Microbiology* 1999, 145(11):3245-3253.
21. Byun S G, Kim M D, Lee W H, Lee K J, Han N S, Seo J H: Production of GDP-L-fucose, L-fucose donor for fucosyloligosaccharide synthesis, in recombinant *Escherichia coli*. *Applied Microbiology and Biotechnology* 2007, 74(4):768-775.
22. Stelling J, Klamt S, Bettenbrock K, Schuster S, Gilles E D: Metabolic network structure determines key aspects of functionality and regulation. *Nature* 2002, 420(6912): 190-193.
23. Klamt S, Gagneur J, von Kamp A: Algorithmic approaches for computing elementary modes in large biochemical reaction networks. *IEE Proceedings Systems Biology* 2005, 152(4):249-255.
24. Urbanczik R, Wagner C: An improved algorithm for stoichiometric network analysis: theory and applications. *Bioinformatics* 2005, 21(7):1203-1210.
25. Ruffing A, Chen R R: Metabolic engineering of microbes for oligosaccharide and polysaccharide synthesis. *Microbial Cell Factories* 2006, 5:25.
26. Dumon C, Samain E, Priem B: Assessment of the two *Helicobacter pylori* α-1,3 fucosyltransferase ortholog genes for the large scale synthesis of LewisX human milk oligosaccharides by metabolically engineered *Escherichia coli*. *Biotechnology Progress* 2004, 20(2):412-419.
27. Fierfort N, Samain E: Genetic engineering of *Escherichia coli* for the economical production of sialylated oligosaccharides. *Journal of Biotechnology* 2008, 134(3-4):261-265.
28. Lee S Y: High cell-density culture of *Escherichia coli*. *Trends in Biotechnology* 1996, 14(3):98-105.
29. Zhao J, Baba T, Mori H, Shimizu K: Global metabolic response of *Escherichia coli* to gnd or zwf gene-knockout, based on $^{13}$C-labeling experiments and the measurement of enzyme activities. *Applied Microbiology and Biotechnology* 2004, 64(1):91-98.

We claim:
1. A composition comprising a recombinant microorganism wherein the microorganism expresses a phosphomannomutase (Man B) polynucleotide, a mannose 1-phosphate guanylytransferase (Man C) polynucleotide, a GDP-D-mannose-4,6-dehydratse (Gmd) polynucleotide and a GDP-4-keto-6-deoxymannose 3,5-epimerase 4-reductase (WcaG) polynucleotide; and comprises a heterologous α-1,2 fucosyltransferase polynucleotide, wherein the α-1,2 fucosyltransferase polynucleotide is a *Helicobacter pylori* polynucleotide, wherein the recombinant microorganism overexpresses α-1,2 fucosyltransferase, and wherein 2'-fucosyllactose can be produced at an amount of 2.5 or more g/L.

2. The composition of claim 1 wherein the microorganism is a bacteria or yeast.

3. The composition of claim 2 wherein the bacteria is *Escherichia coli* and the yeast is *Saccharomyces cerevisiae*.

4. The composition of claim 3 wherein the *Escherichia coli* is DH5α strain or JM strain.

5. The composition of claim 4 wherein the *Escherichia coli* is JM strain.

6. The composition of claim 1, wherein the microorganism has weak β-galactosidase activity.

7. The composition of claim 1, wherein at least one of the phosphomannomutase (Man B) polynucleotide, mannose 1-phosphate guanylytransferase (Man C) polynucleotide, GDP-D-mannose-4,6-dehydratse (Gmd) polynucleotide and GDP-4-keto-6-deoxymannose 3,5-epimerase 4-reductase (WcaG) polynucleotide is a heterologous polynucleotide.

8. The composition of claim 1, wherein the recombinant microorganism is *Escherichia coli*.

9. The composition of claim 1, wherein the recombinant microorganism is a bacterium.

10. The composition of claim 9, wherein the recombinant microorganism overexpresses an *Escherichia coli* phosphomannomutase (Man B) polynucleotide, an *Escherichia coli* mannose 1-phosphate guanylytransferase (Man C) polynucleotide, an *Escherichia coli* GDP-D-mannose-4,6-dehydratse (Gmd) polynucleotide, an *Escherichia coli* GDP-4-keto-6-deoxymannose 3,5-epimerase 4-reductase (WcaG) polynucleotide, or combinations thereof, and wherein the α-1,2 fucosyltransferase polynucleotide is a *Helicobacter pylori* polynucleotide.

11. A method for producing 2'-fucosyllactose (2-FL) in a microorganism, comprising i) providing the microorganism of claim 1; ii) fermenting the microorganism in the presence of lactose; and iii) collecting 2-FL from the microorganism or from a culture broth of the microorganism.

12. The method of claim 11 wherein the microorganism is a bacteria or yeast.

13. The method of claim 12 wherein the bacteria is *Escherichia coli* and the yeast is *Saccharomyces cerevisiae*.

14. The method of claim 13 wherein the *Escherichia coli* is DH5a strain or JM strain.

15. The method of claim 14 wherein the *Escherichia coli* is JM strain.

16. The method of claim 15 wherein the JM strain *Escherichia coli* overexpresses at least one of a phosphomannomutase (Man B) polynucleotide, a mannose 1-phosphate guanylytransferase (Man C) polynucleotide, a GDP-D-mannose-4,6-dehydratse (Gmd) polynucleotide and a GDP-4-keto-6-deoxymannose 3,5-epimerase 4-reductase (WcaG) polynucleotide.

17. The method of claim 11 wherein the presence of lactose is at a concentration of more than 0.5 g/l.

18. The method of claim 11 wherein the presence of lactose is at a concentration of between 0.5 g/l to 15 g/l.

19. The method of claim 11 wherein the method of claim 11 further comprises purifying the 2-FL collected from the microorganism or from the culture broth of the microorganism by filtering through a purification column.

20. The method of claim 19 wherein the purification column is an activated charcoal and celite column.

21. The method of claim 11, wherein the lactose is converted into the 2'-fucosyllactose (2-FL) at a rate of greater than about 0.1 g of 2-FL per gram of lactose.

22. The method of claim 11, wherein the microorganism has weak β-galatosidase activity.

* * * * *